(12) United States Patent
Sun

(10) Patent No.: US 6,847,846 B2
(45) Date of Patent: Jan. 25, 2005

(54) COMPUTER MOUSE FOR ELECTRONIC THERAPY

(76) Inventor: Chia-Chi Sun, P.O. Box No. 6-57, Chung-Ho, Taipei 235 (TW)

( * ) Notice: Subject to any disclaimer, the term of this patent is extended or adjusted under 35 U.S.C. 154(b) by 408 days.

(21) Appl. No.: 10/176,625

(22) Filed: Jun. 24, 2002

(65) Prior Publication Data

US 2003/0236559 A1 Dec. 25, 2003

(51) Int. Cl.[7] .............................. A61N 1/18; A61N 1/26
(52) U.S. Cl. ......................... 607/46; 128/907; 345/156; 345/163; 607/145
(58) Field of Search .............................. 607/46, 72, 76, 607/145, 146; 128/907; 345/156, 163

(56) References Cited

U.S. PATENT DOCUMENTS 6,323,841 B1 * 11/2001 Lai ............................ 345/163
6,599,259 B2 * 7/2003 Muir ........................... 601/46
2004/0189606 A1 * 9/2004 Powpong ..................... 345/163

FOREIGN PATENT DOCUMENTS

JP           2002014769 A  *  1/2002   ........... G06F/3/033

* cited by examiner

Primary Examiner—Carl Layno

(57) ABSTRACT

A computer mouse for electronic therapy includes at least a computer mouse main body disposed with a metal conduction tab, an oscillation circuit, an amplification circuit, an electric current control circuit, an electric connector and a connector; via the oscillation circuit, the amplification circuit and the electric current control circuit, the electric connector obtains power from a host computer end and generates a strong pulse of electric current to transmit to the conduction tab for stimulating an acupuncture point on a user's hand portion; another connector disposed on the main body joins with an externally connected conduction tab for stimulating the acupuncture points on other parts of the body so as to improve the user's health and work efficiency.

6 Claims, 5 Drawing Sheets

COMPUTER MOUSE FOR ELECTRONIC THERAPY

BACKGROUND OF THE INVENTION

1) Field of the Invention

The present invention relates to a computer mouse for electronic therapy combining the function of a conventional computer mouse and an electronic acupuncture device into one unit and utilizing an electric connector to provide power and a circuit to modulate as well as generate a strong electric current pulse to be transmitted by a conduction tab for stimulating a user's acupuncture points so as to increase a health oriented function to the originally convenient operation of the computer mouse.

2) Description of the Prior Art

Countless products utilizing computer mouse devices are available on the market, such as a rolling-ball type computer mouse, an optical computer mouse and a wireless transmission computer mouse; the designs of most of the abovementioned products improve the outer shape of the computer mouse, the detecting method and the control of the key position; those improvements merely increase the fluentness in using the computer mouse.

The present invention of a computer mouse for electronic therapy not only preserves the fluentness of using the computer mouse, but also utilizes multiple internal circuits to generate a strong electric current pulse to be transmitted via a conduction tab to directly stimulate the acupuncture points on a user's hand portion, such as points of Zhongchong, Laogong, Shaofu, and Shaosheng, to furthur stimulate the distal nerves to achieve a relaxing effect. Furthermore, the present invention connects an external conduction tab to stimulate the points of acupuncture on the user's whole body, such as Jianjing and Zusanli to achieve the resting effect for health caring purpose through combining the computer mouse with an electronic acupuncture device.

SUMMARY OF THE INVENTION

The primary objective of the present invention is to increase the application of an electric connector interface and transmit the electric power to a computer mouse device through the electric connector interface for modulating an electric current pulse onto a conduction tab so as to stimulate the points of acupuncture.

Another objective of the present invention is to utilize the conduction tab on the computer mouser and the electric current pulse of an externally connected conduction tab to stimulate the points of acupuncture on the user's hand portion and the other body parts to achieve the effect similar to an electronic acupuncture.

To enable a further understanding of the structural features and the technical contents of the present invention, the brief description of the drawings below is followed by the detailed description of the preferred embodiment.

DETAILED DESCRIPTION OF THE PREFERRED EMBODIMENTS

Figure 1:
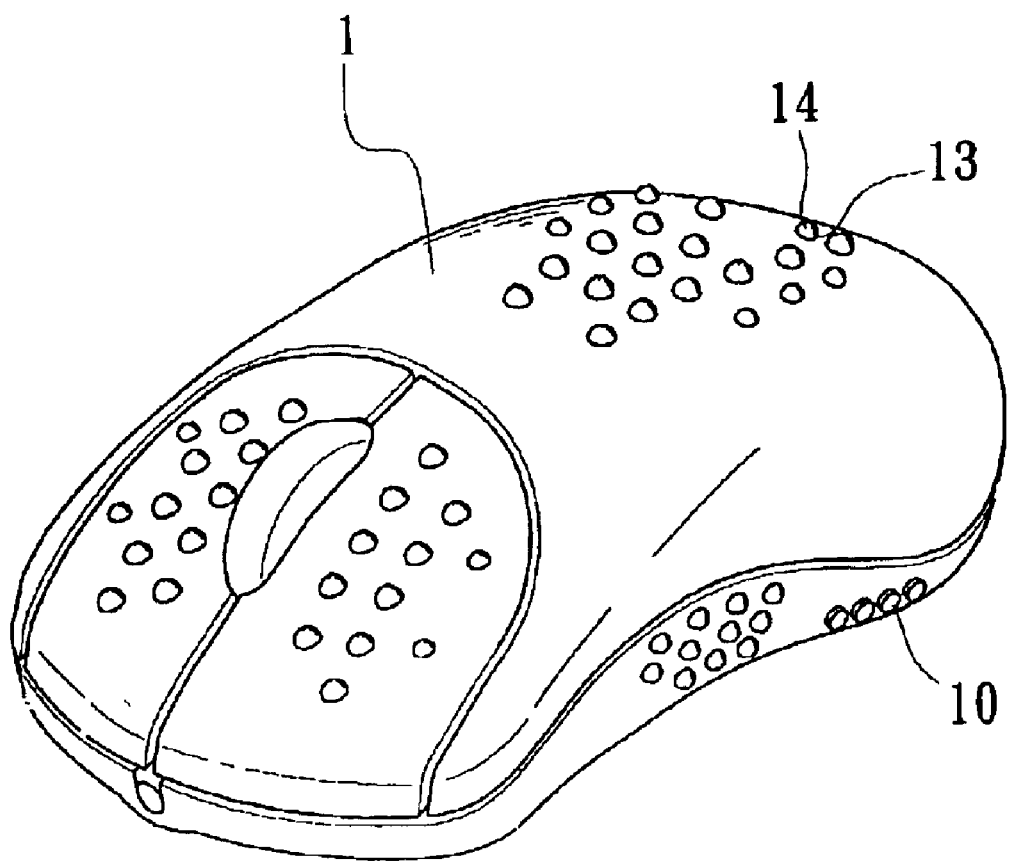
FIG. 1 is a pictorial drawing of the assembly of the structure of a computer mouse of the present invention.

FIG. 1 shows the pictorial drawing of the assembly of the structure of a computer mouse; as indicated, the inventor has designed many through holes (13) on a conventional computer mouse (1) to facilitate convex points (14) on a conduction tab to penetrate an outer case for a user to touch; furthermore, a control key (10) is designed to dispose on the left side of the computer mouse (1) for adjusting the strength of the electric current.

Figure 2:
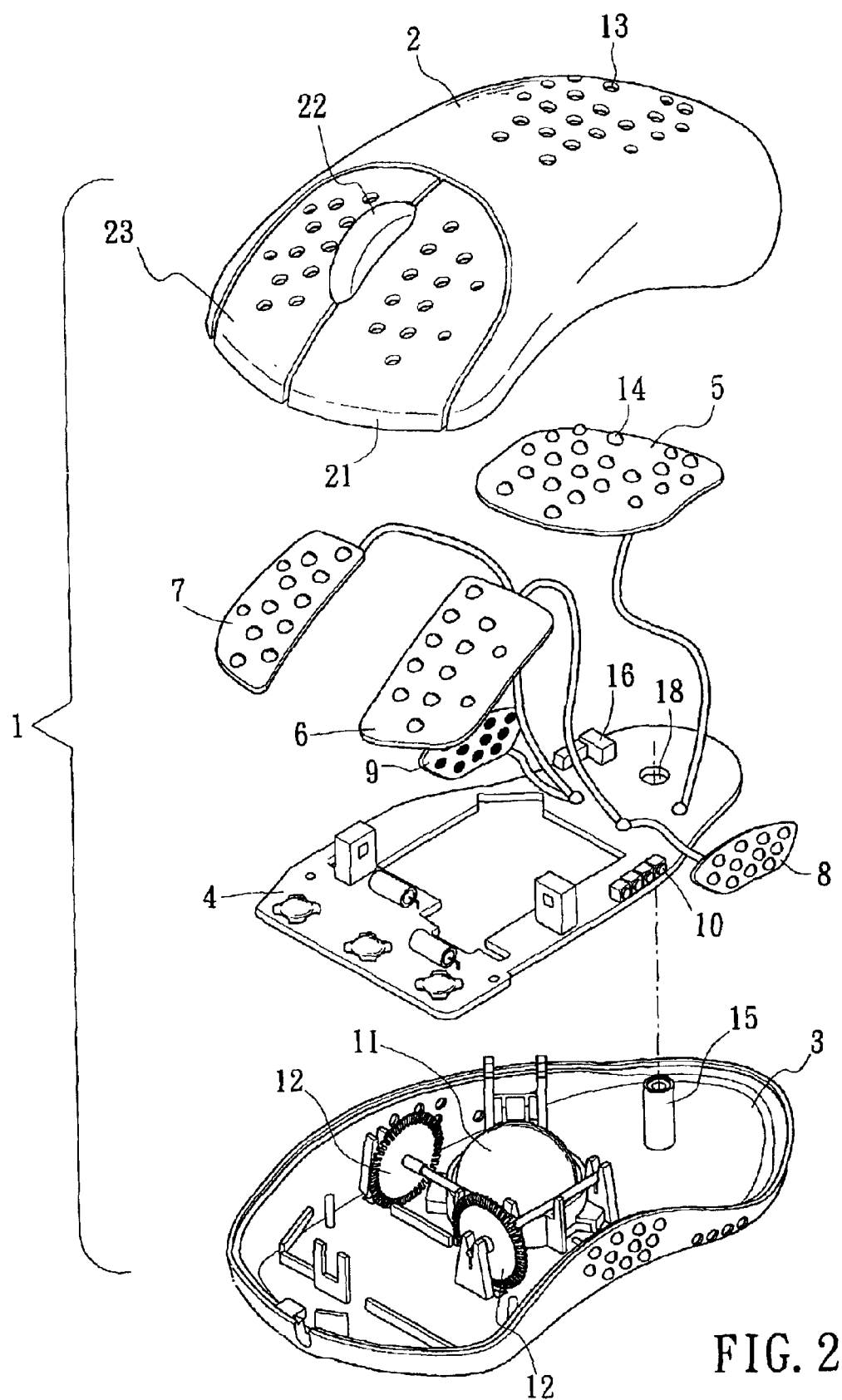
FIG. 2 is a pictorial and exploded drawing of the structure of a computer mouse of the present invention.
Figure 4:
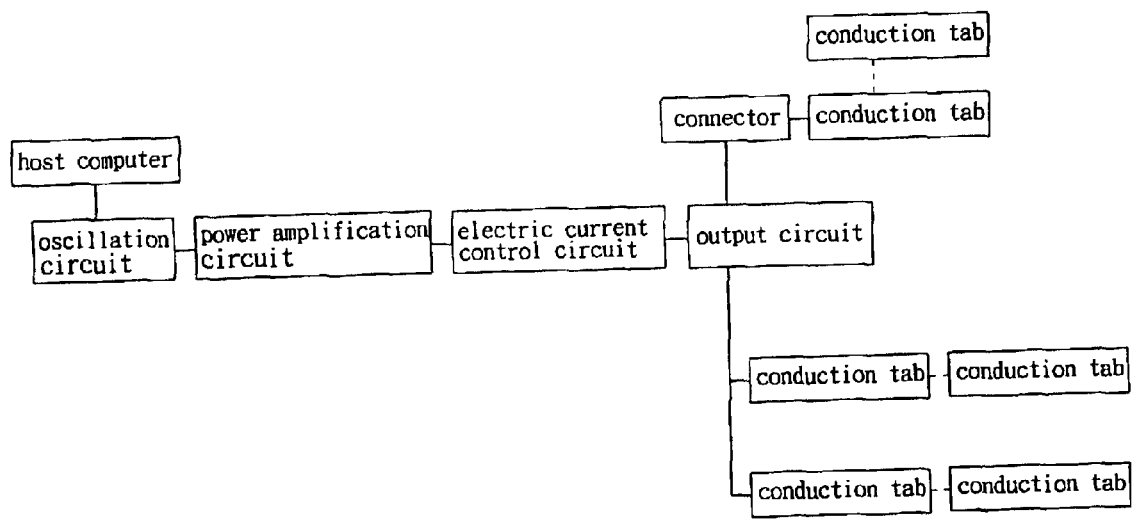
FIG. 4 is a schematic drawing of the circuit of the structure of a computer mouse of the present invention.

FIG. 2 shows the pictorial and exploded drawing of the structure of a computer mouse device (1) of the present invention; the present invention comprises an upper cover plate (2), a lower cover plate (3), a circuit board (4), five conduction tabs (5, 6, 7, 8, 9), a rolling ball (11) and a gear shaft (12), wherein the circuit board (4), as shown in FIG. 4 of the schematic drawing of the circuit of the structure of a computer mouse device (1) of the present invention, comprises an oscillation circuit, a power amplification circuit, a control circuit, an output circuit and a connector (16). The host computer end transmits the power to the oscillation circuit inside the computer mouse device (1) via an electric connector interface to generate the electric current of opposite phase; then the amplification circuit amplifies the little electric current to an acceptable big electric current which is then adjusted by the user to an electric current with a proper strength through the electric current control circuit; finally, the output circuit sends the electric current onto the conduction tabs (5, 6, 7, 8, 9) or the connector (16) sends it onto an externally connected conduction tab (17).

The upper cover plate (2) comprises a left key (2-1), a middle key (2-2), a right key (2-3) and a plurality of through holes (13); the screw hole post (15) on the lower cover plate (3) inserts into the through hole (18) to connect with the lower cover plate (3) into one unit; wherein the convex points (18) on the conduction tab (5, 6, 7, 8, 9) penetrate through the outer case to become touch points; the rolling ball (11) and the gear shaft (12) are the basic structures of a computer mouse device (1) and disposed on the lower cover plate (3) for moving the computer mouse device (1) and calculating the displacement.

Figure 3:
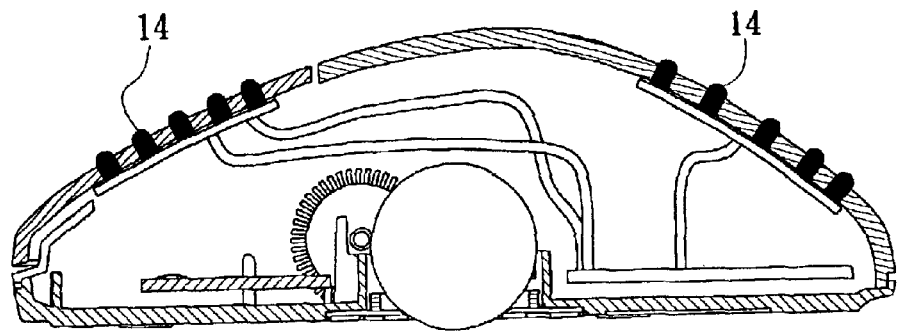
FIG. 3 is a lateral and cross-sectional drawing of the structure of a computer mouse of the present invention.

FIG. 3 shows the lateral and cross-sectional drawing of the structure of a computer mouse device (1) of the present invention; the convex points (14) are designed to dispose on the front and the rear portions of the computer mouse device (1) as suitable portions for the user's hand to touch.

Figure 5:
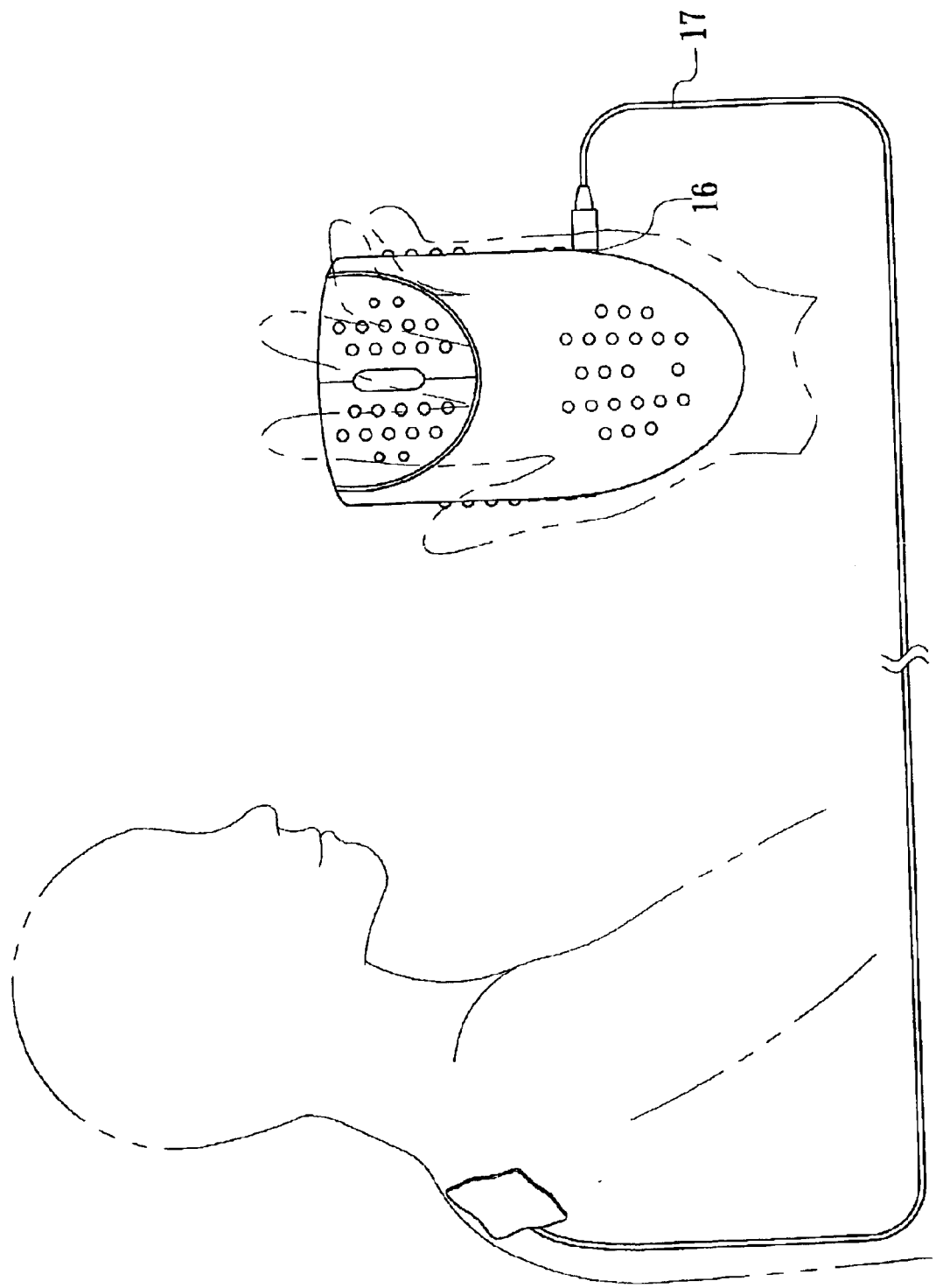
FIG. 5 is a drawing of using a conduction tab of the structure of a computer mouse of the present invention.

FIG. 5 shows the drawing of using a conduction tab of the structure of a computer mouse device (1) of the present invention; the connection between the connector (16) and the external conduction tab (17) stimulates the points of acupuncture on the user's body.

Figure 6:
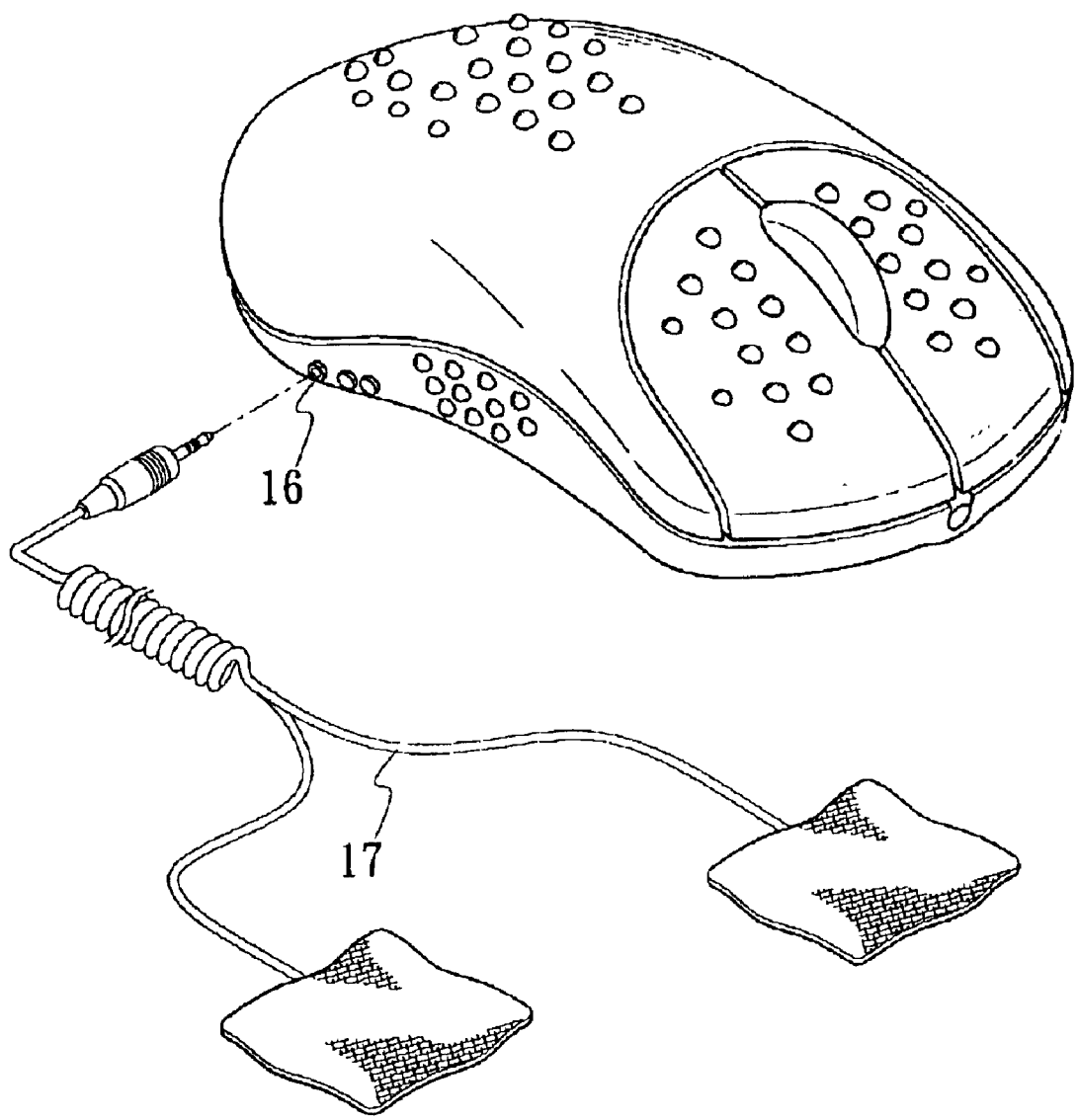
FIG. 6 is a drawing of the engagement between an externally connected conduction tab and the structure of a computer mouse of the present invention.

FIG. 6 shows the drawing of the engagement between an externally connected conduction tab (17) and the structure of a computer mouse device (1) of the present invention; via the connector (16), the external conduction tab (17) engages with the computer mouse device (1).

It is of course to be understood that the embodiment described herein is merely illustrative of the principles of the invention and that a wide variety of modifications thereto may be effected by persons skilled in the art without departing from the spirit and scope of the invention as set forth in the following claims.

What is claimed is:

1. A computer mouse for electronic therapy comprises a computer mouse main body disposed with a metal conduction tab, an external conduction tab, an oscillation circuit, an amplification circuit and an electric current control circuit; via the oscillation circuit, the amplification circuit and the electric current control circuit, the computer mouse for electronic therapy obtains power from a host computer end through an electric connector to generate a strong pulse of electric current to transmit to the conduction tab for stimulating an acupuncture point on a hand portion by applying the Chinese ancient principles of acupuncture; furthermore, through the function of the connector, the user utilizes the external conduction tab to stimulate the points of acupuncture on the whole body; wherein, the conduction tab is situated at the lower aspect of an upper cover plate, convex points of the conduction tab penetrate through holes on the upper cover plate to become the touch points for massaging the points of acupuncture; a screw hole post joins the upper cover plate and a lower cover plate into one unit to become the main body of the computer mouse device; the external conduction tab obtains power through the connector to stimulate the other points of acupuncture on the other parts of the body.

2. The computer mouse for electronic therapy according to claim 1, wherein via an electronic connector interface, the computer mouse device directly obtains power from the host computer end; the electric connector is a Universal Series Bus (USB) connector.

3. The computer mouse for electronic therapy according to claim 1, wherein at least one conduction tab is disposed therein and provided for a user to touch the penetrated convex points.

4. The computer mouse for electronic therapy according to claim 1, wherein at least one circuit board is included for converting the direct electric current into an adjustable electric current pulse.

5. The computer mouse for electronic therapy according to claim 1, wherein the computer mouse device is designed to have at least one connector for engaging with the external conduction tab.

6. The computer mouse for electronic therapy according to claim 1, wherein the external conduction tab has at least one conduction tab.

* * * * *